(12) United States Patent
Abbott et al.

(10) Patent No.: US 9,360,478 B2
(45) Date of Patent: Jun. 7, 2016

(54) MONITORING AN IMMUNOASSAY

(75) Inventors: Timothy John Abbott, Oxfordshire (GB); David Patrick Edward Brookes, Oxfordshire (GB)

(73) Assignee: COZART BIOSCIENCE LIMITED, Oxfordshire (GB)

( * ) Notice: Subject to any disclaimer, the term of this patent is extended or adjusted under 35 U.S.C. 154(b) by 509 days.

(21) Appl. No.: 12/665,501

(22) PCT Filed: Jun. 19, 2008

(86) PCT No.: PCT/GB2008/050466
§ 371 (c)(1),
(2), (4) Date: Apr. 12, 2010

(87) PCT Pub. No.: WO2008/155579
PCT Pub. Date: Dec. 24, 2008

(65) Prior Publication Data
US 2010/0206055 A1    Aug. 19, 2010

(30) Foreign Application Priority Data
Jun. 20, 2007   (GB) .................................. 0711932.4

(51) Int. Cl.
*G01N 33/558* (2006.01)
*G01N 33/543* (2006.01)

(52) U.S. Cl.
CPC ........ *G01N 33/558* (2013.01); *G01N 33/54306* (2013.01)

(58) Field of Classification Search
CPC ..................... G01N 33/558; G01N 33/54306
USPC ................................................ 73/53.01, 147
See application file for complete search history.

(56) References Cited

U.S. PATENT DOCUMENTS 3,485,295 A * 12/1969 Hrdina .......................... 165/147
3,688,574 A *  9/1972 Aruntunian et al. ....... 73/861.05

(Continued)

FOREIGN PATENT DOCUMENTS

DE   19628562 A1   1/1998
DE   196 39 227    3/1998

(Continued)

OTHER PUBLICATIONS

Office Action, dated Jun. 27, 2012, issued in corresponding Japanese Application No. 2010-512778.

(Continued)

*Primary Examiner* — John Fitzgerald
(74) *Attorney, Agent, or Firm* — Saul Ewing LLP

(57) ABSTRACT

A method of monitoring an immunoassay comprises determining the position of the flow edge of fluid across an immunoassay region. This allows, for example, early detection of possible errors in the test. For example the speed of the movement of the fluid flow edge may be determined from measurements of the position of the fluid flow edge at times throughout the test, and the determined speed may be compared with one or more thresholds to determine whether the test is proceeding correctly. A further method of monitoring an immunoassay comprising monitoring the variation with time of a reference zone of an immunoassay region. This can provide the user with early information as to whether the test is proceeding correctly. The above methods may also be used to provide methods to improve the run conditions of a test during its development. The method may be applied to a competitive assay.

17 Claims, 2 Drawing Sheets

(56) References Cited

U.S. PATENT DOCUMENTS

| | | | |
|---|---|---|---|
| 3,693,436 A * | 9/1972 | Gildner | 73/861.05 |
| 3,892,492 A * | 7/1975 | Eichenberger | 356/434 |
| 3,941,477 A | 3/1976 | Schodl et al. | |
| 4,094,647 A * | 6/1978 | Deutsch et al. | 435/4 |
| 4,399,362 A | 8/1983 | Cormier et al. | |
| 4,420,566 A | 12/1983 | Jessop et al. | |
| 4,523,853 A | 6/1985 | Rosenbladt et al. | |
| 4,559,831 A * | 12/1985 | Prestele | 73/861.05 |
| 4,616,653 A | 10/1986 | Samson et al. | |
| 4,857,453 A * | 8/1989 | Ullman et al. | 435/7.92 |
| 4,995,402 A | 2/1991 | Smith et al. | |
| 5,047,351 A | 9/1991 | Makiuchi et al. | |
| 5,049,487 A | 9/1991 | McGarraugh et al. | |
| 5,114,350 A | 5/1992 | Hewett et al. | |
| 5,145,789 A | 9/1992 | Corti et al. | |
| 5,170,438 A * | 12/1992 | Anger et al. | 382/100 |
| 5,179,288 A | 1/1993 | Miffitt et al. | |
| 5,304,468 A | 4/1994 | McGarraugh et al. | |
| 5,316,727 A | 5/1994 | Suzuki et al. | |
| 5,344,754 A | 9/1994 | Zweig et al. | |
| 5,355,735 A * | 10/1994 | Miller et al. | 73/861.05 |
| 5,504,013 A | 4/1996 | Senior | |
| 5,580,794 A | 12/1996 | Allen | |
| 5,679,584 A | 10/1997 | Mileaf et al. | |
| 5,686,659 A | 11/1997 | Neel et al. | |
| 5,786,220 A | 7/1998 | Pronovost et al. | |
| 5,795,543 A | 8/1998 | Strahs et al. | |
| 5,817,526 A * | 10/1998 | Kinoshita et al. | 436/526 |
| 5,837,546 A | 11/1998 | Allen et al. | |
| 5,885,839 A | 3/1999 | Goins et al. | |
| 5,889,585 A | 3/1999 | Markart | 356/39 |
| 5,922,284 A * | 7/1999 | Kinoshita et al. | 422/68.1 |
| 5,968,835 A | 10/1999 | Tsugura et al. | |
| 5,968,839 A | 10/1999 | Blatt et al. | |
| 6,055,060 A | 4/2000 | Bolduan et al. | |
| 6,156,271 A | 12/2000 | May et al. | |
| 6,194,222 B1 * | 2/2001 | Buechler et al. | 436/518 |
| 6,222,619 B1 | 4/2001 | Herron et al. | |
| 6,235,241 B1 | 5/2001 | Catt et al. | |
| 6,361,956 B1 | 3/2002 | Hänninen et al. | |
| 6,399,398 B1 | 6/2002 | Cunningham et al. | |
| 6,448,067 B1 | 9/2002 | Tajnaföi et al. | |
| 6,454,726 B1 | 9/2002 | Catt et al. | |
| 6,581,438 B1 * | 6/2003 | Hall et al. | 73/53.01 |
| 6,613,580 B1 | 9/2003 | Chow et al. | 436/180 |
| 6,707,554 B1 | 3/2004 | Miltner et al. | |
| 6,796,164 B2 * | 9/2004 | McLoughlin et al. | 73/28.01 |
| 6,825,918 B2 | 11/2004 | Eisenmann et al. | |
| 6,830,731 B1 | 12/2004 | Buechler et al. | |
| 6,847,451 B2 | 1/2005 | Pugh et al. | |
| 6,949,221 B2 | 9/2005 | Kiser et al. | |
| 6,951,631 B1 | 10/2005 | Catt et al. | |
| 7,018,847 B2 | 3/2006 | Mendel-Hartvig et al. | |
| 7,022,271 B2 * | 4/2006 | Suganuma | 264/40.4 |
| 7,070,920 B2 * | 7/2006 | Spivey et al. | 435/4 |
| 7,109,042 B2 | 9/2006 | May et al. | |
| 7,154,593 B2 | 12/2006 | Eisenmann et al. | |
| 7,262,857 B2 * | 8/2007 | Koike | 356/445 |
| 7,274,829 B2 * | 9/2007 | Wada et al. | 382/274 |
| 7,315,378 B2 | 1/2008 | Phelan et al. | |
| 7,317,532 B2 * | 1/2008 | Sharrock et al. | 356/436 |
| 7,616,315 B2 | 11/2009 | Phelan et al. | |
| 7,803,633 B2 * | 9/2010 | Spivey et al. | 436/164 |
| 8,184,848 B2 * | 5/2012 | Wu et al. | 382/100 |
| 8,486,717 B2 * | 7/2013 | O'Farrell et al. | 436/514 |
| 8,623,635 B2 * | 1/2014 | Nazareth et al. | 435/287.1 |
| 8,804,105 B2 * | 8/2014 | Ayliffe | 356/72 |
| 2001/0020589 A1 | 9/2001 | Kopf-Sill | 204/451 |
| 2001/0030741 A1 | 10/2001 | Herron et al. | 356/39 |
| 2001/0034068 A1 * | 10/2001 | Spivey et al. | 436/518 |
| 2002/0192833 A1 * | 12/2002 | Pan et al. | 436/164 |
| 2003/0180815 A1 | 9/2003 | Rawson et al. | |
| 2004/0152208 A1 | 8/2004 | Hutchinson et al. | |
| 2004/0152209 A1 | 8/2004 | Zin et al. | |
| 2005/0037511 A1 * | 2/2005 | Sharrock | G01N 21/251 436/164 |
| 2005/0196875 A1 | 9/2005 | Blatt et al. | 436/514 |
| 2005/0267569 A1 * | 12/2005 | Barrett et al. | 623/1.44 |
| 2006/0003396 A1 * | 1/2006 | Spivey et al. | 435/7.92 |
| 2006/0008896 A1 * | 1/2006 | Nazareth et al. | 435/287.2 |
| 2008/0213875 A1 * | 9/2008 | Sharrock | G01N 21/8483 435/288.7 |
| 2008/0287316 A1 * | 11/2008 | Spivey et al. | 506/12 |
| 2009/0031830 A1 * | 2/2009 | Kolp et al. | 73/866.3 |
| 2009/0133480 A1 * | 5/2009 | Ivanov et al. | 73/64.51 |
| 2010/0172802 A1 * | 7/2010 | Sharrock | G01N 21/8483 422/82.05 |
| 2011/0003392 A1 * | 1/2011 | Stayton et al. | 436/86 |
| 2011/0178723 A1 * | 7/2011 | Sharrock | G01N 21/8483 702/32 |
| 2011/0223673 A1 * | 9/2011 | Profitt | 436/8 |
| 2013/0065321 A1 * | 3/2013 | Nazareth et al. | 436/500 |
| 2013/0183199 A1 * | 7/2013 | Wang et al. | 422/82.05 |
| 2014/0377879 A1 | 12/2014 | Phelan et al. | |

FOREIGN PATENT DOCUMENTS

| | | |
|---|---|---|
| EP | 0 157 525 A1 | 10/1985 |
| EP | 0291194 A1 | 11/1988 |
| EP | 0 349 215 | 1/1990 |
| EP | 0362809 A1 | 4/1990 |
| EP | 0653625 A1 | 5/1995 |
| EP | 0 819 943 | 7/1997 |
| EP | 0819943 A2 | 7/1997 |
| EP | 0728309 B1 | 8/1997 |
| EP | 0826777 A1 | 3/1998 |
| EP | 0833145 A1 | 4/1998 |
| EP | 0782707 B1 | 11/1998 |
| EP | 1046122 A1 | 10/2000 |
| EP | 1 484 611 A2 | 8/2004 |
| EP | 1 602 929 | 12/2005 |
| FR | 2 383 441 | 10/1978 |
| GB | 2 302 733 | 1/1997 |
| GB | 2365526 A | 2/2002 |
| GB | 2 402 475 | 12/2004 |
| JP | 06-230009 | 8/1994 |
| JP | 2000258418 A | 9/2000 |
| JP | 2002-501179 T | 1/2002 |
| JP | 2002310903 A | 10/2002 |
| JP | 2003-004743 | 1/2003 |
| JP | 2007-040939 | 2/2007 |
| WO | 9404925 A1 | 3/1994 |
| WO | 9513542 A1 | 5/1995 |
| WO | 9609546 A1 | 3/1996 |
| WO | 9825143 A1 | 6/1998 |
| WO | 9935602 A1 | 7/1999 |
| WO | WO 99/35602 | 7/1999 |
| WO | WO 00/04381 | 1/2000 |
| WO | 0019185 A1 | 4/2000 |
| WO | 0210713 A2 | 2/2002 |
| WO | 2004070353 A2 | 8/2004 |

OTHER PUBLICATIONS

Combined Search and Examination Report, dated Nov. 21, 2011, issued in related UK Application No. GB1119423.0.
Examination Report, dated Feb. 10, 2011, issuedi n related UK Application No. GB0711932.4.
Office Action, dated Dec. 18, 2012, and its English translation, issued in corresponding Japanese Application No. 2010-512778.
English translation of Office Action, dated Jan. 29, 2015, in corresponding Japanese Application No. 2013-086550.
International Search Report, dated Nov. 7, 2008, issued in International Application No. PCT/GB2008/050466.
Search Report, dated Oct. 29, 2007, issued in priority GB Application No. GB0711932.4.
Supplemental Search Report, dated Dec. 21, 2007, issued in priority GB Application No. GB0711932.4.
"Predictor pregnancy test" [online], published Jul. 1, 2005, dooyoo. Available from http://web.archive.org/web/20050701084137/http://www.dooyoo.co.uk/parenting-issues-predictor-pregnancy-test/1007282.

(56) References Cited

OTHER PUBLICATIONS

European Search Report issued in Application No. EP 04 25 3076, Jul. 3, 2006.
Search Report issued in French Application No. 04 06067, Jul. 3, 2006.
European Search Report issued in Application No. EP 04 25 3077, Jul. 11, 2006.
Search Report issued in French Application No. 04 06065, Jul. 11, 2006.
European Search Report issued in Application No. EP 04 25 3078, Jul. 14, 2006.
Search Report issued in French Application No. 04 06066, Jul. 14, 2006.
Search Report issued in Application No. GB 0312801.4, Dec. 1, 2003.
Search Report issued in Application No. GB 0312802.2, Dec. 1, 2003.
Search Report issued in Application No. GB 0312815.4, Dec. 1, 2003.
"Amended Complaint", *Inverness Medical Innovations, Inc.*, et al., v. *Church & Dwight Company, Inc.*, Case No. 1:10-cv-10027-DPW, U.S. District Court, District of Massachusetts, Jul. 20, 2010.

* cited by examiner

MONITORING AN IMMUNOASSAY

CROSS REFERENCE TO RELATED APPLICATIONS

This application claims the priority of PCT/GB2008/050466, filed on Jun. 19, 2008, which claims priority to Great Britain Application No. 0711932.4, filed Jun. 20, 2007, the entire contents of which are hereby incorporated in total by reference.

BACKGROUND OF THE INVENTION

The present invention relates to a method of monitoring an immunoassay test, in particular to monitoring the quality of an immunoassay test while the test is being carried out. This makes it possible for a user to, if necessary, adjust one or more parameters of the test while it is being run to improve the conditions under which the test is run.

As is known, an immunoassay test may be used to detect the presence of particular compounds, such as drugs, in the body. Known methods of testing include immunoassay "strip" testing where an antibody is labelled with a visible marker, and is drawn along a membrane passing over test zones (or "active zones") and a control zone impregnated with analyte conjugate substances or other binding substances. The presence of particular compounds in the sample are detected by a visible change occurring the in the corresponding zone of the strip owing to the interaction of the labelled antibodies and the conjugate substances resulting in visible lines forming on the strip in some of the zones. The colour formed may, depending on the assay format, be proportional or inversely proportional to analyte concentration in the fluid sample.

In one such test a sample of bodily fluid, such as blood, sweat, urine or saliva, is placed at an upstream end of an immunoassay region, which is normally in the form of a strip, and is drawn along the strip by capillary action. One zone of the strip, at or near the upstream end of the strip, contains an antibody for a particular drug labelled (conjugated) with a suitable marker. When the sample of bodily fluid passes through this zones, the particular drug will, if it is present in the sample of bodily fluid, bind with the antibody. The strip further comprises one or more active zones which contain a drug-protein derivative specific to the drug that is being tested for. When the sample of bodily fluid passes over the active zones, because the antibody-marker conjugate has already bound to the drug in the sample, it is not free to bind with the drug-protein derivative bonded on the target region of the strip. However, if the particular drug is absent from the sample of bodily fluid, the antibody-marker conjugate will be free to bind with the drug-protein conjugate in the active zones, causing the antibody-marker conjugate to become immobilised at the site of the drug-protein conjugate in the active zones. As a result, a visible marker is deposited in the active zones, as a coloured line or stripe.

In practice, a typical immunoassay strip will include a number of active zones, each containing a drug-protein derivative specific to a respective drug to allow more than one drug to be tested for.

A typical immunoassay strip further includes a control region at or near its downstream end. When the sample of bodily fluid reaches the control region a known reaction leading to a visible indication, for example a colour change, occurs. When the visible indication occurs in the control zone, this indicates that the sample of fluid has passed along the length of the strip to the control zone and that the test has been successfully run. The visible indication in the control zone may also be used in calibrating the results obtained in the various active zones of the strip.

The active zones and control zones are normally separated by background zones that contain no drug-protein conjugate.

The part of the strip extending from the region on which the fluid sample is placed to the control zone constitutes the "active area of the strip". An end pad may be placed downstream of the active region to absorb any fluid that reaches the downstream end of the active region.

Immunoassay tests of this nature are well-known. Mobile screening devices that can perform such an immunoassay test are also known, for example for use at the roadside, in a sporting stadium etc. In general, mobile devices comprise some form of reader, into which is inserted an immunoassay cartridge. The immunoassay cartridge consists, in general, of an immunoassay strip contained in a suitable housing. A sample of bodily fluid may be placed on one end of the immunoassay strip, by means of an entry port provided in the housing of the cartridge.

One example of an immunoassay reader is disclosed in WO 00/04381. A fuller description of the immunoassay process is contained therein.

A first aspect of the present invention provides a method of monitoring the quality of an immunoassay, the method comprising determining the position of the flow edge of fluid across an immunoassay region;
   determining a value of a parameter representing variation with time of the position of the flow edge of fluid across the immunoassay region; and
   obtaining information about the quality of the immunoassay from the value of the parameter.

In a conventional method of performing an immunoassay, the test fluid is required to traverse the entire length of the immunoassay strip before the strip is examined to determine whether physical markers have been deposited in any of the active regions. It takes a finite time for fluid to traverse along the length of the active area of the strip; in fact, it is normal to leave the strip for a time of period, known as the "incubation time", after the fluid has travelled the length of the strip to the control zone. Thus, the strip is not normally examined before a time equal to the incubation time plus the time required for fluid to travel along the length of the active area of the strip has lapsed. A normal time for fluid flow from initial detection to reaching the end pad might be tens of seconds or so, and a total incubation might be a couple of minutes. If, as an example, the police are carrying out a roadside check on a driver, the driver is unavoidably detained for at least this time, even if the results of the test eventually indicate that the driver is in a legally fit state to drive. Moreover, if the test should not work satisfactorily, this is not known until the end of the incubation period.

SUMMARY OF THE INVENTION

The present invention therefore proposes obtaining information from the immunoassay strip as the fluid is passing across the active area of the strip. This makes possible, for example, an early determination as to whether the test is proceeding satisfactorily or whether an error has occurred in the test.

It is known to monitor an immunoassay test in order to obtain an early indication of whether the test will give a positive or negative result. This is suggested in, for example, GB 2402475.

However, it has not previously been proposed to monitor an immunoassay test while the test is underway in order to obtain qualitative information as to whether the test is proceeding satisfactorily.

GB 2302733 discloses using the total time to reaction completion to determine whether the result of the test is positive or negative. This document again does not suggest monitoring an immunoassay test while the test is underway in order to obtain information as to whether the test is proceeding satisfactorily.

EP 1602929 discloses using a separate label to determine the speed of fluid flow. The determined speed is used to adjust the final static value of the test once the immunoassay itself has completed. However, this document again does not suggest monitoring the immunoassay test while the test is underway in order to obtain information as to whether the test is proceeding satisfactorily.

In a preferred embodiment, the method comprises obtaining a correction for the performance of the test from the determined value of the parameter. The correction may be applied automatically, or the user may be prompted to make the correction. As an example the correction may be to vary the incubation time of the test. Other possible corrections include applying heat to a test cartridge whilst using appropriate controls, automatically altering some other physical aspect of the test such as by automatically applying a run solution to an immunoassay strip to encourage capillary flow, or prompting the user to take action such as adding more sample or adjusting the angle of tilt of the immunoassay strip at which the test is being conducted.

A second aspect of the present invention provides a method of monitoring an immunoassay, the method comprising monitoring the shape of the flow edge of fluid across an immunoassay region.

A third aspect of the present invention provides a method of monitoring the quality of an immunoassay, comprising monitoring the variation with time of a reference zone of an immunoassay region, to obtain an early indication as to whether the test is proceeding satisfactorily or not.

Further aspects and embodiments of the present invention are set out in the remaining claims.

BRIEF DESCRIPTION OF THE DRAWINGS

Preferred embodiments of the present invention will now be described by way of illustrative example with reference to the accompanying figures in which.

DETAILED DESCRIPTION

Figure 1:
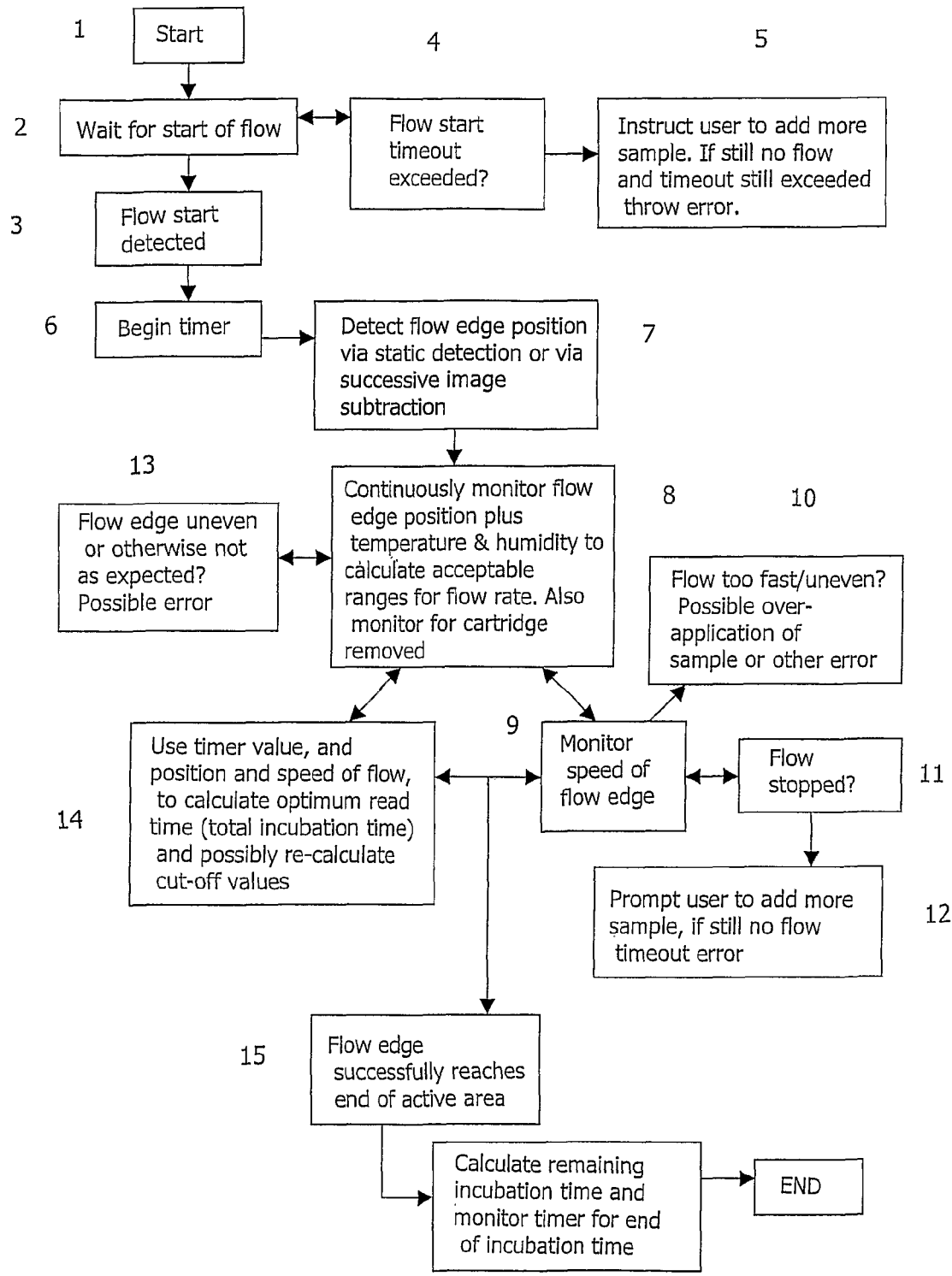
FIG. 1 is a block flow diagram of a method according to a first embodiment of the present invention.

Monitoring the flow of fluid across an immunoassay strip or region during an immunoassay test has many advantages. These include providing early confirmation that a test has run, or is running, correctly, making possible the automatic start of an incubation timer that sets the duration of the incubation period, and making possible the calculation of an optimum time at which to read the results of the test.

The present invention provides a method of monitoring the quality of an immunoassay, while the immunoassay is in progress. The method comprises determining the position of the flow edge of fluid across an immunoassay region, and determining a value of a parameter representing the variation with time of the position of the flow edge of fluid across the immunoassay region. This provides qualitative information about the progress of the immunoassay. It is therefore possible to provide the user with early information as to whether the immunoassay is proceeding satisfactorily.

The method further comprises obtaining information about the quality of the immunoassay from the value of the parameter. If the value of the parameter indicates that the progress of the immunoassay is not satisfactory, it may be possible to provide a correction to the performance of the immunoassay that will allow successful completion of the immunoassay.

As an example, the parameter may be the speed of movement of the flow edge of fluid across the immunoassay strip. If the speed is found to be too low, this would indicate that the test is not proceeding satisfactorily; one possible correction in this case would be to prompt the user to add more sample. Alternatively, the correction may be to vary the incubation time of the test. Other possible corrections that may be made include applying heat to a test cartridge (for example where the cartridge is provided with a heater to enable the temperature of the immunoassay strip to be increased), automatically altering (ie without requiring action from the user) some other physical aspect of the test for example by automatically applying a run solution to encourage capillary flow, or prompting the user to take action such as adding more sample or adjusting the angle of tilt of the immunoassay.

Information about the quality of the immunoassay may be obtained simply by comparing the determined value of the parameter with one or more reference values. In an example where the parameter is the speed of movement of the fluid flow edge, the determined value may be compared with one threshold that indicates a lower limit of the range of desirable speeds and with a second threshold that indicates an upper limit for the range of desirable speeds.

As is explained in more detail below, it may be desirable to take into account one or more environmental factors (such as the temperature or humidity) when comparing the parameter with the threshold(s).

In an alternative embodiment, rather than comparing the value of the parameter with a threshold, the determined value of the parameter could be input to a look-up table which outputs one or more desired correction factors to the test. As explained in more detail below one possible correction that may be made is to adjust the value of the incubation time and, in such a case, values of the incubation time may be stored in a look-up table, with the measured value of the parameter being input to the look-up table to determine the appropriate incubation time.

The present invention thus makes it possible to correct the performance of the test itself, to ensure that it is carried out correctly. As a result, the present invention allows the immunoassay to be carried out more reliably, and may also avoid the need to adjust the results of an immunoassay after it has been carried out to compensate for the manner in which the test was performed.

Possible parameters that may be used in a method of the present invention include, but are not limited to, the time before movement of the flow edge of fluid is detected, speed of movement of the fluid flow edge across the immunoassay region, a change in speed of movement of the fluid flow edge, and the total time required for the fluid flow edge to cross the immunoassay region. Other parameters that may be used include the shape of flow edge of the fluid, and the variation in time of the area of the test strip in which flow is present and the area of the test strip in which flow is not present, as these may provide more information than a more simple measurement of the position of the flow edge.

FIG. 1 shows in detail one example of a method according to the present invention. In the example of FIG. 1, the time interval before the start of fluid flow is detected is used to monitor the performance of the immunoassay.

Initially the method is started at step 1, for example by introducing a test sample of bodily fluid onto an immunoassay region, for example an immunoassay strip. The method may be carried out in, for example, any immunoassay reader generally similar to that disclosed in WO 00/04381. There is then a step 2 of waiting for the start of fluid flow along the immunoassay strip, until the start of fluid flow is detected at step 3.

At step 4 it is determined whether the time interval between the start of the process at step 1 and the detection of the start of fluid flow at step 3 exceeds a pre-determined threshold. If it is determined that the time interval exceeds the threshold, this indicates that there may be a problem with the test. The method may then alert the user, for example by instructing the user to add more sample at step 5. If adding more sample does not result in the start of fluid flow, this indicates that there may be an error with the test, and a suitable error message may be displayed. Alternatively, a correction may be made automatically, without requiring action from the user, for example automatically applying a run solution to the immunoassay strip to encourage capillary flow.

If it is determined that the interval between the start of the process at step 1 and the detection of the start of fluid flow at step 3 is less than the pre-set threshold, this provides an indication that the test is proceeding correctly. A timer may then be started, at step 6, to measure the time lapsed since the detection of the start of fluid flow.

In one embodiment of the invention, the flow of fluid along the immunoassay strip is determined throughout the test, by detection of the flow edge position—this is shown at step 7. The detection of the position of the flow edge may be performed in any convenient manner. For example, flow edge detection may be performed by obtaining images of the active area of the immunoassay strip at successive times, and subtracting one image from the other. The output of the subtraction process may preferably be high-pass filtered, to enhance any peaks in the resultant subtraction image. Additionally or alternatively, a thresholding process may be applied to the subtraction image, to determine whether any of the features in the subtraction image exceed a pre-set threshold.

Alternatively, a "static" edge detection approach may be used, in which the fluid flow edge is detected in a single image.

The invention is not, however, limited to monitoring the fluid flow across the immunoassay strip by determining the position of the fluid flow edge. Another technique that may be used is to determine the boundary between the part of the immunoassay strip that is "wet" (that is, is covered by fluid) and the part of the strip that is "dry" (that is, has not yet been reached by the test fluid). The position of the boundary at a particular time may be determined from an image acquired at that time, or by comparing images obtained at different times. The shape of the fluid flow edge may also be determined.

The position of the fluid flow edge is preferably monitored continuously over the duration of the test that is being performed, as indicated at step 8. This allows the speed of movement of the fluid flow edge along the strip to be determined, at step 9; the speed of movement of the flow edge may be determined simply by determining the location of the fluid flow edge at two different times, and dividing the distance travelled by the time elapsing between one image and the other. This also allows a change in the speed of movement to be detected.

It should be noted that, in practice, images of the immunoassay strip will be acquired at discrete times. Images of a developing immunoassay might be taken anywhere from several every second, to every second or one every few seconds, depending on the expected speed of the fluid flow. As a result the position of the fluid flow edge can be determined only for the times at which images are acquired. The term "continuously", as used herein, is intended to cover determination of the position of the fluid flow edge at discrete times at which images are available.

The determined speed of movement of the fluid flow edge may be compared with one or more pre-determined thresholds. For example, the determined speed may be compared, at step 10, with a threshold that represents the upper limit of the desirable speed of movement of the fluid flow edge. A determination that the speed of movement of the fluid flow edge exceeds an upper threshold would indicate the presence of an error in the test and the user may be alerted. Determination that the speed of movement of the fluid flow edge exceeds an upper threshold might indicate, for example, possible over-application of the sample of fluid. Alternatively, determination that the speed of movement of the fluid flow edge exceeds an upper threshold might indicate that the viscosity of the fluid is too low, and that the fluid may have been adulterated with water.

The determined speed of movement of the fluid flow edge may additionally or alternatively be compared with a threshold that indicates a lower limit of the range of desirable speeds for the fluid flow edge. A determination, at step 11, that the determined speed is below the lower threshold could indicate that the flow of fluid along the immunoassay strip has stopped. If it is found that the flow of fluid along the strip has stopped, the user may be prompted to add more sample, at step 12, or a run solution to encourage capillary flow may be automatically applied. If adding further fluid does not lead to a re-start of fluid flow, this may suggest that there is an error with the test, and the user can be informed of the error. For example, a determination that the speed is too low might indicate that the sample is too viscous, which could show incorrect sample addition or that the sample is bad.

It should be noted that the speed of movement of the fluid flow edge along the immunoassay strip will generally depend on environmental factors such as the ambient temperature and humidity. The method therefore preferably comprises taking at least one environmental factor into account in the step of comparing the observed speed of movement of the fluid flow edge with the upper and/or lower reference values. For example, the method may comprise monitoring the ambient temperature and/or humidity, and determining acceptable upper and/or lower thresholds for the speed of movement of the fluid flow edge at the measured value of the temperature and/or humidity. Alternatively, the upper and/or lower thresholds for the speed of movement of the fluid flow edge may be fixed, and the measured speed of the fluid flow edge may be adjusted in dependence on the measured values of temperature and/or humidity before comparison with the fixed reference value(s).

The tilt of the reader is another factor that may influence the measured speed of movement of the fluid flow edge. In a further embodiment the reader may comprises a tilt sensor or accelerometer for measuring the tilt of the reader, and the measured tilt may be taken into account when comparing the measured speed of movement of the fluid flow edge with the threshold(s).

Although the description of taking at least one environmental factor into account is with particular reference to the observed speed of movement of the fluid flow edge, it is generally preferable to compensate for environmental factors such as temperature and/or humidity and/or tilt of the reader when the invention makes use of parameters other than the speed of movement of the fluid flow edge. Furthermore, in embodiments in which the determined parameter representing the variation with time of the fluid flow edge is not compared with one or more thresholds but is input into a look-up table to obtain a correction, it is again preferable that the parameter is corrected for factors such as temperature and/or humidity and/or tilt of the reader before being input into the look-up table. Alternatively, the look-up table may store details of the required correction against one or more environmental parameter as well as against the parameter representing variation with time of the position of the flow edge of fluid—in this case, the value of the environmental parameter(s) are also input into the look-up table.

The method may further comprise monitoring the shape of the fluid flow edge, at step 13. If the shape of the fluid flow edge is uneven, or is otherwise not as expected, this may indicate a possible error in the test and the user may again be informed.

In this connection, it should be noted that an uneven fluid flow edge may introduce errors into the determination of the speed of movement of the fluid flow edge in methods that involve determining the position of the fluid flow edge at two successive times, giving apparently abnormal flow rates and other such problems. Determining the position of the fluid flow edge by finding the boundary between the "wet" area of the immunoassay strip and the "dry" of the strip is less susceptible to errors caused by an uneven flow edge; however, such methods are generally more complex to perform than methods that involve determining the position of the fluid flow edge.

In addition to monitoring the speed of movement of the fluid flow edge and/or the shape of the fluid flow edge, the method of the invention may also be used to monitor for other errors, such as the removal of the cartridge containing the immunoassay strip from the reader.

The knowledge of the position of the fluid flow edge, the speed of movement of the fluid flow edge, and the elapsed time may be used at step 14 to calculate the expected time taken for the fluid flow edge to reach the end of the active area of the immunoassay strip, and hence to determine the optimum read time for the test. For example, if the speed of movement of the fluid flow edge is comparatively quick, this might indicate that the active areas may develop less well than had the flow been slower. Therefore, in addition to obtaining information about the quality of the immunoassay while it is in progress, the level at which the reader decides between a positive and a negative result (this is referred to as the "cut-off") may also be adjusted based on the detected flow rate.

Additionally or alternatively, determination of the cut-off may be based on the development of the reference area—a stronger reference zone might mean a higher threshold for test zones, or vice-versa depending on the application.

The position of the fluid flow edge may be monitored throughout the test, until it is determined at step 15 that the fluid flow edge has successfully reached the end of the active area (for example, that it has reached the control zone present at the downstream end of the active area of the immunoassay strip).

Once the fluid flow along the active area of the strip has been completed, the acquired data, for example the time required for the flow edge to reach the end of the active area, can be used to enhance the test in various ways such as, for example, calculating the optimum incubation time for the test, and from this determining the remaining incubation time. The timer may then be monitored to determine the end of the incubation period. The data may also be used to dynamically re-assign cut-offs.

The method of FIG. 1 has been described in the context of a test having a single immunoassay strip. It will however be apparent to a person skilled in the art that the method may be applied to a test having multiple test strips and so having multiple areas of flow of sample fluid. Where a particular test has multiple areas of flow, the method of FIG. 1 may be applied to every flow area or, if desired, to selected ones of the flow areas. This allows, for example, the relative flow rates of two test areas to be monitored and compared with one another, and the results of this comparison may be used to advise the user of any action required, to modify any internal parameters of the test, or to indicate that an error has occurred. For example, the speeds of movement of the fluid flow edge on two different test areas may be measured and compared with one another, and the user may be alerted if the difference between the two measured flow rates, or the ratio between the two measured flow rates, exceeds a pre-determined threshold on the assumption that this indicates an error in one of the tests.

The present invention may also be applied to competitive assays, in which the relative and/or absolute speed of movement of the fluid flow edge itself gives the results of the test. In a competitive assay the relative viscosity, or at least ability to flow in a given assay, gives rise to the speed at which the fluid sample flows. A separate reference area of flow is also monitored, and the difference in speed of flow, and/or the total relative flow times, is used to determine the result. For example if a there is a lot of binding in an assay (e.g. an assay specially developed for this purpose), this will increase the viscosity and make the flow in the test zones slower than in the reference zones. A cut-off might, for example, be "under 10 seconds difference in flow times=negative, over 10 seconds positive"; or "greater than 5 mm/s peak flow rate difference=positive, flow rate difference never greater than 5 mm/s=negative".

It should be noted that FIG. 1 shows only one embodiment of the present invention, and many other variations are possible. For example, it would be possible to perform the step of determining the shape of the fluid flow edge independently of the step of measuring the speed of movement of the fluid flow edge.

Figure 2:
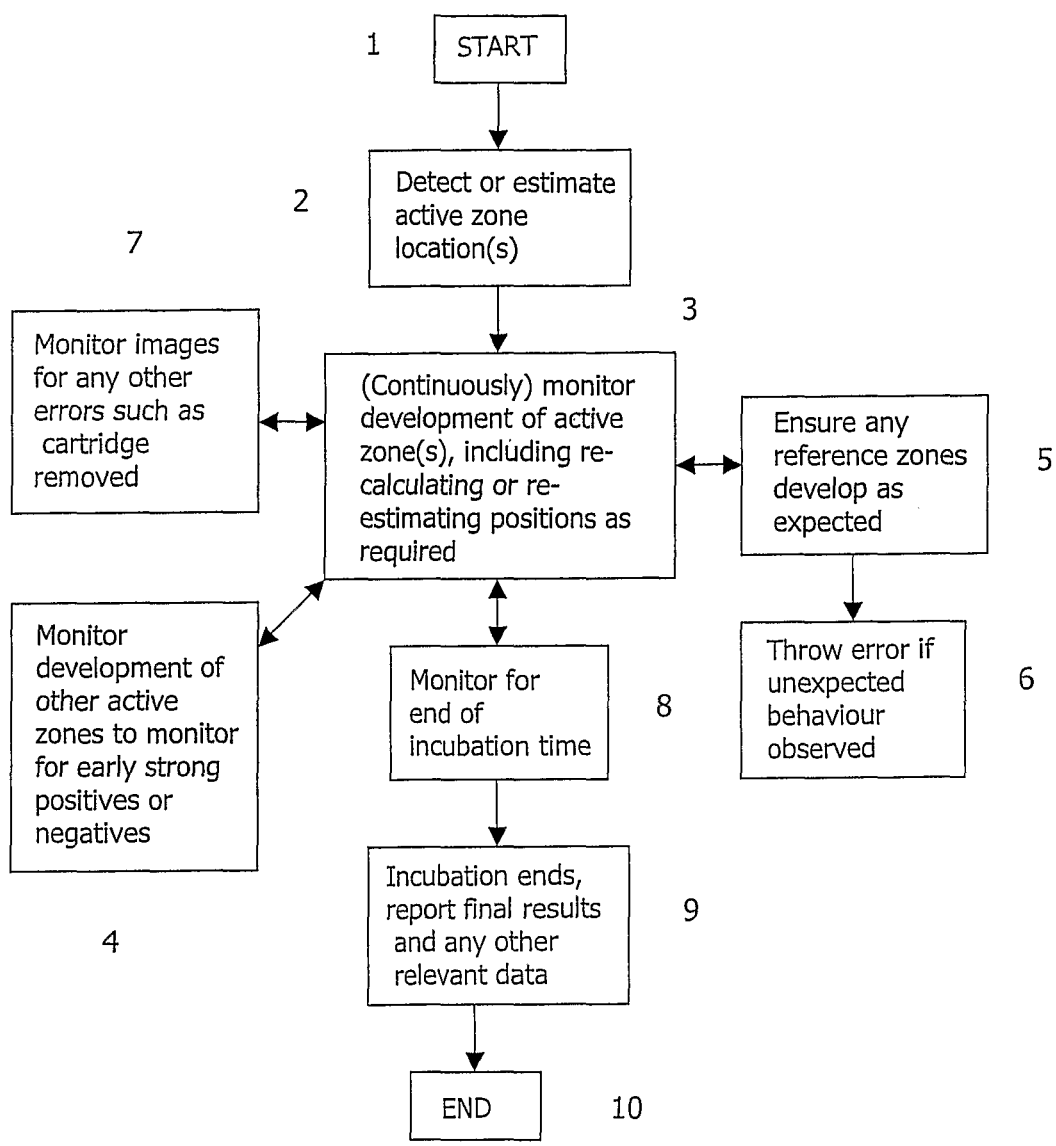
FIG. 2 is a block flow diagram of a method according to a second embodiment of the present invention.

The method of FIG. 1 is directed primarily to determining whether an immunoassay test is being carried out correctly. FIG. 2 shows a further embodiment of the present invention, and this is again directed primarily to providing a user with early information about the quality of the test. This achieved by monitoring the variation with time of a feature of an immunoassay region, for example monitoring the variation with time of a reference zone of the immunoassay strip. If the monitoring suggests that the reference zone is developing in an unexpected way, the user may be alerted of this before the test is complete.

The method of FIG. 2 is started at step 1 by a user placing a test sample of bodily fluid on an immunoassay strip. At step 2, the location of one or more areas of the immunoassay strip that it is desired to monitor are detected or estimated, using any suitable technique. FIG. 2 illustrates the case where the location of one or more reference zones of the immunoassay strip are determined at step 2, but the invention is not limited to this.

At step 3, the development of the selected features is monitored, preferably continuously. Where the selected feature is a reference zone, the monitoring may consist of monitoring, for example, at least one of the colour, opacity or reflectivity of the active zone.

If the results of monitoring the selected feature suggest that its location was not estimated correctly at step 2, the position may be re-calculated or re-estimated as necessary.

In addition to monitoring the selected features, other features of the immunoassay strip, such as active zones, may also be monitored during the test, at step 4.

The one or more control zones (reference zones) are monitored during the test, at step 5. As explained, monitoring one or more reference zones makes it possible to check that the reference zone(s) are developing as would be expected. If the monitoring shows that one or more reference zones are not developing as expected, and unexpected behaviour is observed, an error indication may be sent at step 6.

The method may also comprise monitoring images of the immunoassay strip for indications that other errors have occurred, such as inadvertent or premature removal of the cartridge from the reader (step 7).

The invention may further comprise monitoring for the end of the incubation time, at step 8. This may be done using a timer, or by monitoring a reference feature until it achieves a pre-set level or shows no further signs of changing.

At step 9, once the incubation period has ended, final results of the test and any other relevant data (for example the ambient temperature, humidity) may be reported to the user, and the method ends at step 10.

It should again be noted that FIG. 2 shows only one possible method, and variations are possible. For example, the step of monitoring one or more reference zone(s) to determine whether they develop as expected may be performed independently of monitoring one or more active zones.

The method of FIG. 2 has again been described with reference to a test that uses a single immunoassay strip. The invention is not, however, linked to this, but may be applied to a test having two or more immunoassay strips, by monitoring one or more selected features in each of two or more immunoassay strips.

The present invention may be performed by any suitably adapted immunoassay reader. For example, the reader of WO 00/04381 is able to obtain an image of the active area of an immunoassay strip, by illuminating the active area of the strip with light from a suitable light source and recording light reflected from the strip using a suitable recording device (for example a charge coupled device). The reader of WO 00/04381 may be arranged to put the invention into effect by arranging it to record images of the active area of the immunoassay strip at time intervals throughout the test, and determining the position of the fluid flow edge using one or more of the recorded images, or monitoring one or more features of the immunoassay strip in the acquired images. The reader of WO 00/04381 may further be provided with a suitable controller for carrying out the methods of the invention, for example for comparing a determined speed of the movement of the fluid flow edge against one or more pre-set thresholds, or determining a parameter of a feature of the immunoassay strip, such as the colour or opacity of an active zone, at intervals throughout the test.

The invention claimed is:

1. A method of monitoring the quality of an immunoassay, the method comprising:
    determining, using an image processing device configured to determine positions of flow edges of fluid across immunoassay regions, a position of a flow edge of fluid across an immunoassay region;
    obtaining a value of a parameter representing variation with time of the position of the flow edge of fluid across the immunoassay region;
    determining information about the quality of the immunoassay from the value of the parameter; and
    applying a correction for performing of a test from the obtained value of the parameter.

2. A method as claimed in claim 1 and comprising applying the correction using a look-up table.

3. A method as claimed in claim 1 wherein the parameter is selected from the group consisting of: a time before movement of the flow edge of fluid is detected, a speed of movement of the fluid flow edge, a change in speed of movement of the fluid flow edge and a time for the fluid flow edge to cross the immunoassay region.

4. A method as claimed in claim 1 and further including a step of determining when the flow edge of fluid reaches a boundary of an active area of the immunoassay region.

5. A method as claimed in claim 1 and further comprising monitoring a shape of the flow edge of fluid.

6. A method as claimed in claim 1 and comprising monitoring a variation with time of an area of the immunoassay region containing fluid.

7. A method as claimed in claim 1 and comprising a step of determining a start of movement of the flow edge of fluid across the immunoassay region.

8. A method as claimed in claim 7 and comprising taking an observed time for the fluid flow edge to reach the boundary into account in a determination of an incubation period for the immunoassay.

9. A method as claimed in claim 1 and further comprising determining a position of another flow edge of fluid across another immunoassay region.

10. A method as claimed in claim 9 and comprising comparing a speed of movement of the fluid flow edge across the immunoassay region with a speed of movement of the fluid flow edge across the another immunoassay region.

11. A method as claimed in claim 9 and comprising comparing the travel time of the fluid flow edge across the immunoassay region with the travel time of the another fluid flow edge across the another immunoassay region.

12. A method as claimed in claim 1 and comprising comparing the obtained value of the parameter with a reference.

13. A method as claimed in claim 12 and comprising taking at least one environmental factor into account in the step of comparing the obtained value of the parameter with the reference.

14. A method as claimed in claim 13 wherein the at least one environmental factor comprises an ambient temperature.

15. A method as claimed in claim 13 wherein the at least one environmental factor comprises an ambient humidity.

16. A method as claimed in claim 13, wherein the at least one environmental factor comprises a tilt of the immunoassay region.

17. An immunoassay reader device having a processor configured to:
    determine a position of a flow edge of fluid across an immunoassay region;
    obtain a value of a parameter representing variation with time of the position of the flow edge of fluid across the immunoassay region;
    determine information about the quality of the immunoassay from the value of the parameter; and
    apply a correction for performing of a test from the obtained value of the parameter.

* * * * *